United States Patent [19]

Rosenberg

[11] Patent Number: 5,531,219
[45] Date of Patent: Jul. 2, 1996

[54] USE OF LIQUID FLUOROCARBONS TO FACILITATE PULMONARY DRUG DELIVERY

[75] Inventor: Gwen H. Rosenberg, Rancho Santa Fe, Calif.

[73] Assignee: Alliance Pharmaceutical Corp., San Diego, Calif.

[21] Appl. No.: 334,688

[22] Filed: Nov. 4, 1994

[51] Int. Cl.⁶ .................................................. A61M 15/00
[52] U.S. Cl. ...................................... 128/203.12; 128/913
[58] Field of Search ........................ 128/203.12, 204.18, 128/913

[56] References Cited

U.S. PATENT DOCUMENTS

| | | | |
|---|---|---|---|
| 4,927,623 | 5/1990 | Long, Jr. | 424/5 |
| 5,024,995 | 6/1991 | Robertson et al. | 514/21 |
| 5,158,536 | 10/1992 | Sekins et al. | 604/20 |
| 5,306,483 | 4/1994 | Mautone | 424/45 |

FOREIGN PATENT DOCUMENTS 9309270  9/1993  WIPO.

OTHER PUBLICATIONS

Merritt, et al., "Exogenous Surfactant Treatments for Neonatal Respiratory Distress Syndrome and their Potential Role in the Adult Respiratory Distress Syndrome", *Drugs* 38(4): 591–611 (1989).

Nakayama et al., "Pulmonary dysfunction in surgical conditions of the newborn infant", *Crit. Care Med.* 19: 926–933 (1991).

Richman, P. et al. "Lung Lavage with Oxygenated Fluorocarbon Improves Gas Exchange and Lung Compliance in Cats with Acute Lung Injury" *1990 World Conference on Lung Health* (Boston, MA), Abstract.

*Primary Examiner*—Aaron J. Lewis
*Attorney, Agent, or Firm*—Knobbe, Martens, Olson & Bear

[57] ABSTRACT

A multiple method step for delivering a medicament to the lungs, in connection with which, a biocompatible perfluorocarbon liquid is introduced into the lungs and the a microparticulate medicament is introduced into the lungs where it is dispersed into the pulmonary spaces which are filled or coated with the perfluorocarbon liquid.

29 Claims, No Drawings

USE OF LIQUID FLUOROCARBONS TO FACILITATE PULMONARY DRUG DELIVERY

FIELD OF THE INVENTION

The present invention relates to a method for medicament delivery, and specifically relates to the use of biocompatible liquid fluorocarbons to facilitate delivery of medicaments in microparticulate form particularly for treatment of pulmonary and other physiological conditions.

BACKGROUND OF THE INVENTION

A wide variety of delivery systems are available for preventative or therapeutic administration of medicaments. Methods well known in the field include injection (subcutaneous, intravenous, intramuscular or intraperitoneal), delivery via a catheter, diffusion from a patch applied to the skin or a bolus implanted under the skin, intraocular delivery via liquid drops, ingestion of a pill, capsule or gelcap, and inhalation of an aerosol. Aerosol delivery systems generally rely on a mixture of the therapeutically active agent with one or more propellants and inactive ingredients to increase dispersion and stability of the active agent. Inhalation of the aerosol can be via either the nose or mouth and often is self-administered. Because of the small volume of each dosage, the propellant generally evaporates simultaneously or shortly after delivery of the active ingredient.

Fluorocarbons are fluorine substituted hydrocarbon compounds that are biocompatible. Brominated fluorocarbons and other fluorocarbons are also known to be safe, biocompatible substances when appropriately used in medical applications. In addition to their use as aerosol propellants, they have been used in medical applications as imaging agents and as blood substitutes. U.S. Pat. No. 3,975,512 to Long uses fluorocarbons, including brominated perfluorocarbons, as a contrast enhancement medium in radiological imaging.

Gases in general, including oxygen and carbon dioxide, are highly soluble in some fluorocarbons. This characteristic has permitted investigators to develop emulsified fluorocarbons as blood substitutes. For a general review of the use of fluorocarbons as blood substitutes see "Reassessment of Criteria for the Selection of Perfluorochemicals for Second-Generation Blood Substitutes: Analysis of Structure/Property Relationship" by Jean G. Riess, *Artificial Organs* 8:34–56, 1984.

Oxygenatable fluorocarbons act as a solvent for oxygen. They dissolve oxygen at higher tensions and release it as the partial pressure decreases; carbon dioxide is similarly stored and released. When a fluorocarbon is used intravascularly, oxygenation of the fluorocarbon occurs naturally through the lungs. However, the fluorocarbon can be oxygenated prior to use in applications such as percutaneous transluminal coronary angioplasty, stroke therapy and organ preservation.

Liquid breathing using oxygenated fluorocarbons has been demonstrated on several occasions. For example, an animal submerged in an oxygenated fluorocarbon liquid may exchange oxygen and carbon dioxide normally when the lungs fill with the fluorocarbon. Although the work of breathing is increased in total submersion experiments, the animal can derive adequate oxygen for survival by breathing the oxygenated fluorocarbon liquid.

Full liquid breathing as a therapy presents significant problems. Liquid breathing in a hospital setting requires dedicated ventilation equipment capable of handling liquids.

Moreover, oxygenation of the fluorocarbon being breathed must be accomplished separately. The capital costs associated with liquid breathing are considerable. Partial liquid ventilation techniques as disclosed in related U.S. application Ser. No. 07/695,547 are a safe and convenient clinical application of liquid breathing using oxygenated fluorocarbons.

A wide variety of pulmonary conditions exist in humans that are treatable with medicaments. Some conditions result from congenital defects, either as the result of premature birth and inadequate development of the lungs or from genetic abnormalities. One of these is Respiratory Distress Syndrome (RDS) that occurs in premature infants. Other distress conditions result from trauma to the lungs induced by exposure to particulate matter, infectious agents or injury. Adult Respiratory Distress Syndrome (ARDS) results from pulmonary trauma in adults. Infectious agents (bacterial, viral and fungal) can damage lungs by local infections and treatment of such diseases is well known. Immunocompromised patients such as people suffering from Acquired Immunodeficiency Syndrome (AIDS) or people undergoing drug treatment to suppress immunological rejection of transplanted organs also have increased susceptibility to lung infections. Lung cancer also affects thousands of people throughout the world and often results in their death. These diseases reflect only some of a wide variety of medical conditions associated with pulmonary distress.

Lung Surfactant Conditions

Lung surfactant functions to reduce surface tension within the alveoli thus permitting the alveoli to be held open under less pressure. (*The Pathologic Basis of Disease*, Robbins and Cotran eds., W. B. Saunders Co., New York, N.Y. 1979). Lung surfactant covers the lung surfaces, promotes alveolar expansion and mediates transfer of oxygen and carbon dioxide. Surfactant supplementation is beneficial in a number of medical therapies including, for example, for individuals with congenital lung surfactant deficiencies.

Some medical procedures require that fluids be added to the lungs, for example, as a wash to remove endogenous or exogenous matter from patients with asthma, cystic fibrosis or bronchiectasis. Lavage with nonsurfactant liquids such as a physiological saline solution can remove natural lung surfactant, thus increasing lung trauma. Supplementation of lung surfactant may relieve this trauma.

Currently, therapeutic surfactant supplements are used in infants when the amount of lung surfactant present is insufficient to permit proper respiratory function. Surfactant supplementation is most commonly used in Respiratory Distress Syndrome (RDS), a specific form of which is known as hyaline membrane disease, when surfactant deficiencies compromise pulmonary function. Hyaline membrane contains protein-rich, fibrin-rich edematous fluid mixed with cellular debris that impedes gaseous exchange in the lungs. Although RDS is primarily a disease of newborn infants, Adult Respiratory Distress Syndrome (ARDS), an adult form of the disease, has many similar characteristics and lends itself to similar therapies.

RDS affects up to 40,000 infants each year in the United States accounting for up to 5,000 infant deaths annually. The primary etiology of RDS is attributed to insufficient amounts of pulmonary surfactant. Premature infants born before the 36th week of gestation are at greatest risk because of insufficient lung development. Neonates born at less than 28 weeks of gestation have a 60–80% chance of developing RDS which may be a life-threatening condition.

At birth, high inspiratory pressures are required to expand the lungs. When normal amounts of lung surfactant are present, the lungs retain up to 40% of the residual air volume after the first breath. With subsequent breaths, lower inspiratory pressures adequately aerate the lungs because the lungs now remain partially inflated. With low levels of surfactant, whether in infant or adult, the lungs are virtually devoid of air after each breath. The lungs collapse with each breath and the individual must continue to work as hard for each successive breath as she/he did for her/his first. Thus, exogenous therapy is required to facilitate breathing and minimize lung damage.

A premature infant lacks sufficient surfactant necessary to breathe independently at birth. Because the lungs mature rapidly after birth, therapy is often only required for three or four days. After this critical period the lung has matured sufficiently to give the neonate an excellent chance of recovery.

Adult Respiratory Distress Syndrome (ARDS) can occur as a complication of shock-inducing lung trauma, infection, burn or direct lung damage, immune hypersensitivity reactions, hemorrhage, or the inhalation of irritants that injure the lung epithelium and endothelium. Histologically, ARDS presents as diffuse damage to the alveolar wall accompanied by capillary damage. In addition, subsequent hyaline membrane formation creates a barrier to gaseous exchange which results in further loss of lung epithelium leading to decreased surfactant production and foci of collapsed alveoli (atelectasis). This initiates a vicious cycle of hypoxia and lung damage. Tumors, mucous plugs or aneurysms can also induce atelectasis.

In advanced cases of respiratory distress, whether in neonates or adults, the lungs are solid and airless. The alveoli are small and crumpled, while the proximal alveolar ducts and bronchi are overdistended. Hyaline membranes line the alveolar ducts and scattered proximal alveoli.

The critical threat to life in respiratory distress is inadequate pulmonary exchange of oxygen and carbon dioxide resulting in metabolic acidosis. In infants, acidosis together with the increased effort required to bring air into the lungs, is a lethal combination for about 20–30% of affected babies.

Cystic Diseases

Cystic diseases are critical lung diseases that produce abnormally large air spaces in the lung parenchyma. They generally are either congenic bronchogenic cystic disease or alveolar cysts.

Bronchiogenic cysts are rare congenital malformations often associated with cystic disease of the liver, kidney and pancreas. The cystic cavities are either filled with mucinous secretions or air as a consequence of ballooning out under the continued thrust of respiratory pressure. Infection of the cysts, especially those containing secretions, may lead to progressive metaplasia of the epithelium lining the cyst which may result in necrosis and a lung abscess.

Alveolar cysts are more common and may result from congenital abnormal development or from inflammatory disease with fibrosis, aging and deterioration of the alveolar wall. The walls of alveolar cysts are thin and fragile while the surrounding lung tissue is compressed and atelectatic. In fact, alveolar cysts that lose elasticity are blown up like a balloon with each inspiration.

Cyst cavities are often filled with mucinous secretions that serve as prime sites for development of infection which may promote abscess formation resulting in lung collapse or interstitial pulmonary emphysema. Because excessive secretions accumulate in the lungs, they may require lavage treatments to clear them of excess mucinous secretions to facilitate easier breathing and prevent infections. Cystic diseases are progressive in nature leading to deterioration of elastic and reticulin fibers that predisposes the tissue to rupture. Thus, it is important to treat cystic disease both by relieving inhalation stress on the cystic tissue and by treating the frequent infections associated with cysts.

Lung Cancer

Lung cancer accounts for a significant portion (5–8%) of deaths in the U.S. and throughout the industrialized world. Cancers originating in the lungs are generally one of four types: squamous cell carcinoma (about 30–40% of all lung tumors), adenocarcinoma (about 30–40%), large cell anaplastic carcinoma (less than 10%), and small cell anaplastic carcinoma (approximately 20%). Of these, adenocarcinomas and small cell cancers are most dangerous because they tend to metastasize to other sites in the body.

Most lung cancers occur in or on bronchial walls near the branch point into the trachea although adenocarcinomas often occur in the middle to outer third of the lung. Because all of these areas are exposed to carcinogens in the air, they are susceptible to neoplastic development. Exposure to air also makes them treatable by administering chemotherapeutic agents directly into the lungs by inhalation. However, inhalation therapy has limited application because it exposes both the tumor and healthy tissue to highly toxic chemotherapeutic reagents. Furthermore, as tumors grow within the lung, portions of lung tissue may become relatively shielded by the tumor and thus inaccessible to inhalation therapy.

Because of the wide variety of pulmonary diseases and disorders that occur in humans, there is a need for effective ways to deliver medicaments to the lungs. Because the lungs serve as a primary site for exchange of compounds with the blood, pulmonary delivery can also be used to deliver drugs into the blood stream. The present invention has the advantage over current methods of drug delivery because it is a relatively rapid delivery system of medicaments, particularly for delivery to selected pulmonary tissue. Thus the present invention will have widespread therapeutic application.

SUMMARY OF THE INVENTION

According to one aspect of the invention, there is provided a method for pulmonary drug delivery. The method includes introducing into the pulmonary air passages of a mammalian host a volume of perfluorocarbon liquid substantially equivalent to or less than the pulmonary functional residual capacity of the host. The method further includes introducing a powdered or other microparticulate medicament dispersed in a gas into the pulmonary air passages of the host, such that said perfluorocarbon liquid and said medicament are simultaneously present in pulmonary air passages of the host. In one embodiment, a first volume of the perfluorocarbon liquid is introduced prior to introduction of the medicament. In another embodiment, a second volume of perfluorocarbon liquid is introduced into the pulmonary air passages of the host subsequent to administration of the medicament. In yet another embodiment, the medicament is introduced prior to introduction of the perfluorocarbon liquid. Another embodiment includes lavage with a perfluorocarbon liquid performed prior to introduction of the medicament. In one embodiment, the method includes an additional step after the steps of introducing perfluorocarbon liquid and introducing the powdered or microparticulate medicament, that is the removal of the perfluorocarbon liquid from the pulmonary air passages. Preferably, the perfluorocarbon liquid is removed from the pulmonary air passages by evaporation. In another preferred embodiment, the perfluorocarbon liquid is removed from the pulmonary air passages by mechanical means such as aspiration or physical manipulation.

In a preferred embodiment, the volume of introduced perfluorocarbon liquid is equivalent to 0.01% to 100% of the pulmonary functional residual capacity of the host. In another embodiment, the volume of perfluorocarbon liquid is at least about 1%, 2% or 5% of the pulmonary functional residual capacity of the host. Alternatively, the volume of perfluorocarbon liquid is at least 10% of the pulmonary functional residual capacity of the host. In another preferred embodiment, the volume of perfluorocarbon liquid is at least 20% of the pulmonary functional residual capacity of the host. In one embodiment, the volume of perfluorocarbon liquid is not more than about 60% or 75% of the pulmonary functional residual capacity of the host. In another preferred embodiment, the volume of perfluorocarbon liquid is not more than about 40% or 50% of the pulmonary functional residual capacity of the host. In yet another embodiment, the volume of perfluorocarbon liquid is not more than about 15%, 20%, 25% or 30% of the pulmonary functional residual capacity of the host.

In one embodiment, the medicament is an antibiotic. In another embodiment, the medicament is an antiviral. Preferably, the medicament is an antibacterial. In a preferred embodiment, the medicament is an anticancer agent. In one embodiment, the medicament is a surfactant supplement. In another embodiment, the medicament is at least one enzyme. Preferably, the enzyme is a proteinase. In another embodiment, the enzyme is a deoxyribonuclease. The medicament in another embodiment enhances activity of the immune system of the host. In a preferred embodiment, the medicament is an immunosuppressor. In another preferred embodiment, the medicament is a decongestant.

DETAILED DESCRIPTION OF THE INVENTION

The method of the present invention provides for delivery of a medicament to the pulmonary air passages of a mammalian host by a multiple step process involving introduction of a perfluorocarbon liquid into the lungs and introduction of a medicament in microparticulate form. In one embodiment, the first step is introduction of a perfluorocarbon liquid into the lungs followed by a second step of introducing a microparticulate medicament. In another embodiment, the first step is introduction of a microparticulate medicament which is further distributed into the lungs by a second step of introducing a perfluorocarbon liquid into the lungs. Another embodiment of the method involves first, introducing a perfluorocarbon liquid into the lungs, then introducing a microparticulate medicament into the host's lungs, and subsequently introducing a second volume of perfluorocarbon liquid into the lungs. In all of these embodiments, perfluorocarbon liquid can be removed from the lungs by evaporation or by such mechanical means as are typically used in standard lavage procedures, including aspiration or physical manipulation of the patient such as lowering the patient's head to permit the liquid to drain out under the influence of gravity.

By "pulmonary air passages" is meant parts of the lungs normally occupied by air including the pulmonary channels, spaces within the trachea, left and right bronchi, bronchioles and alveoli.

By "mammalian host" is meant humans and other mammals for veterinary or research purposes, including lambs, pigs, rabbits, cats and dogs.

By "microparticulate medicament" is meant a medicament in powdered form, in microcrystalline suspension, in a clathrate with other compounds, in an aerosol, in a gaseous phase, in a nebulized suspension or any other form of small particles that can be suspended in a gas that is well known in the art, with the proviso in one preferred embodiment that it does not include a drug dispersed in an aerosolized perfluorocarbon that is a liquid at body temperature.

By "introduction of a microparticulate medicament" is meant either active inhalation by the host of a medicament in gaseous suspension or passive introduction into the host's lungs by forcing microparticulate medicament dispersed in a gas into the pulmonary air passages.

By "perfluorocarbon liquid" is meant any fluorinated carbon compound with appropriate physical properties of biocompatibility. These properties are generally met by perfluorocarbons having low viscosity, low surface tension, low vapor pressure, and high solubility for oxygen and carbon dioxide making them able to readily promote gas exchange while in the lungs. The perfluorocarbon liquid may be made up of atoms of carbon and fluorine, or may be a fluorochemical having atoms other than just carbon and fluorine, e.g., bromine or other nonfluorine substituents.

It is preferred, however, that the perfluorocarbon have at least 3 or 4 carbon atoms and/or that its vapor pressure at 37° C. is less than 760 torr.

Representative perfluorochemicals include bis(F-alkyl) ethanes such as $C_4F_9CH=CH_4CF_9$ (sometimes designated "F-44E"), $i-C_3F_9CH=CHC_6F_{13}$ ("F-i36E"), and $C_6F_{13}CH=CHC_6F_{13}$ ("F-66E"); cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyl-decahydroquinoline ("FHQ"), F-n-cyclohexylpurrolidine ("FCHP") and F-2-butyltetrahydrofuran ("FC-75" or "RM101").

Brominated perfluorocarbons include 1-bromo-heptadecafluoro-octane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long.

Also contemplated are perfluorocarbons having nonfluorine substituents, such as perfluorooctyl chloride, perfluorooctyl hydride, and similar compounds having different numbers of carbon atoms.

Additional perfluorocarbons contemplated in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example, compounds having the general formula $C_nF_{2n+1}C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" liquids suitable for use in the present invention. Mixtures of fluorocarbons are also contemplated and are considered to fall within the meaning of "fluorocarbon liquids" as used herein. Additional "fluorocarbons" contemplated are those having properties that would lend themselves to pulmonary gas exchange including FC-75, FC-77, RM-101, Hostinert 130, APF-145, APF-140, APF-125, perfluorodecalin, perfluorooctylbromide, perfluorobutyl-tetrahydrofuran, perfluoropropyl-tetrahydropyran, dimethyladamantane, trimethyl-bicyclo-nonane, and mixtures thereof. Preferred perfluorocarbons are characterized by having: (a) an average molecular weight range from about 350 to 570; (b) viscosity less than about .5 centipoise at 25° C.; (c) boiling point greater than about 55° C.; (d) vapor pressure in the range from about 5 to about 75 torr, and more preferably from about 5 to about 50 torr, at 25° C.; (e) density in the range of about 1.6 to about 2 gm/cm$^3$; and (f) surface tensions (with air) of about 12 to about 20 dyne/cm.

The perfluorocarbon liquid is typically introduced into the pulmonary air passages after a period of at least ten to fifteen minutes of breathing pure oxygen. The perfluorocarbon may be conventionally introduced by simply injecting the liquid into and through an endotracheal tube between breaths. Alternatively, it may be delivered as liquid under pressure, as is done during liquid breathing. Moreover, an aerosol of liquid perfluorocarbon may be inhaled either through the nose or the mouth. Partial liquid ventilation techniques using oxygenated fluorocarbons are disclosed in related U.S. application Ser. No. 07/695,547.

The volume of perfluorocarbon liquid introduced into the pulmonary air passages should preferably be substantially equivalent to 0.01% to 100% of the normal pulmonary functional residual capacity (FRC) of the host. By "pulmonary functional residual capacity" is meant the volume of space in the pulmonary air passages at the end of expiration. For different applications, different amounts of perfluorocarbon are preferred. In one embodiment, the volume of perfluorocarbon liquid is at least 1%, 2%, 3% or 5% of the pulmonary FRC of the host. Preferably, the volume of perfluorocarbon liquid is at least 10% of the host's pulmonary FRC. In another embodiment, the volume of perfluorocarbon liquid is at least 20% of the pulmonary FRC of the host. In other preferred embodiments, the volume of perfluorocarbon liquid is not more than 30%, 50% or 75% of the host's pulmonary FRC. Alternatively, the volume of perfluorocarbon liquid is not more than 20% of the pulmonary FRC of the host. The normal pulmonary FRC of the host is calculated by methods well known in the art. It will be appreciated by those skilled in the art that preferred volumes of filling the lungs with perfluorocarbons may be within certain ranges instead of discrete percentages. Thus, preferred embodiments of the invention include administration of perfluorocarbon of 0.01–1%, 0.01–10%, 1–10%, 1–20%, 5–50%, 10–70%, 50–75%, 50–100% and 75–100% of the host's pulmonary FRC, calculated using standard methods known in the art.

Partial filling of the lung with perfluorocarbon: (a) maintains FRC and prevents surface tension-induced alveolar closure during expiration; (b) reduces surface tension along much of the alveolar surface where perfluorocarbon lies against the alveolar lining; and (c) provides a low surface tension medium for exchange of the powdered or other microparticulate drug delivered by inhalation or by forcing a gaseous suspension into the lungs. In one embodiment, the gaseous suspension is introduced by means of a conventional gas ventilation respirator apparatus. By not exceeding the patient's FRC, the barotrauma associated with liquid breathing is avoided and added mechanical stress caused by inhalation or forced introduction of the powdered drug is precluded. Delivery of perfluorocarbon to a single lobe (unilateral) or local portion (lobar, segmental) is also contemplated. In conjunction with perfluorocarbon and medicament treatment, continuous positive pressure breathing using a conventional ventilator may also be employed. This is particularly desirable when perfluorocarbon is maintained in the lungs for facilitated drug delivery over relatively long periods (up to about 3 hours). This may be achieved by using a volume of perfluorocarbon of about 100% of the patient's FRC and/or by using a relatively low vapor pressure perfluorocarbon, because both impede rapid evaporation of the perfluorocarbon.

Some fluorocarbons having relatively high vapor pressure may be useful for drug therapy in which a single dose of drug is rapidly administered such as for those drugs that are quickly absorbed through the lung tissue. However, high vapor pressures render them less suitable for use in facilitated drug delivery in which the drug must remain in the lungs for a longer period of time (hours). Fluorocarbon liquids contemplated for such long-term drug delivery include PFOB, F-nonmame, FDMA, F-adamatane, F66E, Fi36E, PFoCl and PFoH. Lower vapor pressures are additionally important from an economic standpoint because significant percentages of fluorocarbon having high vapor pressure would be lost due to evaporation during longer-term therapies.

Following the perfluorocarbon-facilitated medicament delivery, the perfluorocarbon liquid may be removed from the pulmonary air passages. The preferred technique for this particular purpose is to simply permit the perfluorocarbon to evaporate from the pulmonary air passages. Positive pressure gas ventilation using a conventional ventilator may be used to facilitate evaporation during or after treatment resulting in substantially complete evaporation from the lungs in a time period (determined by the vapor pressure of the perfluorocarbon) on the order of hours for situations in which perfluorocarbon fills a significant fraction of the patient's FRC.

The fluorocarbon of choice should have functional characteristics that would permit its use temporarily for facilitated medicament delivery because it additionally permits inflation of collapsed portions of the lung, gaseous (oxygen and carbon dioxide) exchange and/or serves as a lung surfactant. Fluorocarbons are biocompatible and most are amenable to sterilization techniques. For example, they can be heat-sterilized under pressure (by using an autoclave) or sterilized by radiation. In addition, sterilization by ultrafiltration is also contemplated.

A variety of medicaments may be used as therapeutics using the present invention's method. All must be in a form that is a microparticulate suspension for inhalation or for forced introduction into the lungs. Preferably, powdered medicament is introduced. Powder may be obtained by standard drying and crushing methods or by freeze-drying and dispersal of the medicament in a gas. Inhalation or forced (positive pressure) introduction, either nasal or oral, of the medicaments can be achieved by any of a variety of methods known in the art. These include mechanical suspension by agitation of the medicament in a closed chamber followed by inhalation, or forced introduction of the suspension from an opening in the chamber. Microparticles can be inhaled from standard aerosol delivery systems which are well known in the art. The host may receive a particulate suspension which is placed into an air stream such as by injection of the powdered drug into a positive pressure ventilation tube or into an endotracheal tube at the moment of inspiration or when air is forced into the lungs. Metered dosages may be mechanically injected into such devices. Powdered medicament may be dispersed in air by using the Venturi effect, where air is moved at right angles across a Venturi tube causing the powdered drug to be drawn through the tube and dispersed into the air that is inhaled or mechanically introduced into the lungs. Pulsatile delivery of medicament in a volume of gas and inhalation of the aerosolized bolus is also known in the art as described in PCT published application WO 9407514, and the delivery techniques described therein can be used in the present invention.

Perfluorocarbons can serve as temporary lung surfactants because they are biologically compatible, decrease the surface tension sufficiently within the alveoli, cover the lung surface easily and promote oxygen and carbon dioxide exchange. When used in conjunction with introduction of a powdered or other microparticulate medicament, perfluorocarbon can facilitate delivery of the medicament to the lungs where it is absorbed by lung tissue or where it acts on substances covering the lung tissue such as hyaline membrane or fungal infections. Perfluorocarbon enhanced drug delivery can also be used to deliver drugs systemically by administering the drug to the lungs where translocation across pulmonary membranes takes place, allowing the drug to rapidly enter the blood system.

Therapeutic surfactant supplements delivered via perfluorocarbon, a biocompatible oxygenatable liquid, would benefit individuals who, for any of a variety of reasons, lack normal levels of lung surfactant. Using the present invention, powdered supplemental surfactant can be delivered directly to the affected area of the lungs while allowing normal oxygen/carbon dioxide exchange to continue.

Because perfluorocarbon has at least some of the functional properties of a lung surfactant it can be used in lavage. When combined with introduction of any of a variety of powdered or other microparticulate medicinal substances, lavage can be additionally advantageous.

The method disclosed herein is particularly well suited for treatment of cystic diseases because the perfluorocarbon liquid fills cysts and holds them open in a relatively static position thus relieving the mechanical stress on the cystic tissue. Introduction of powdered antibiotics into the lungs either by inhalation or forced introduction of the drug then is used to directly treat any infection in the cysts.

The method not only relieves stress during inhalation but also concentrates the drug directly at the site of the infection. Because perfluorocarbon are relatively dense compared to body fluids, the perfluorocarbon will tend to sink and fill the cyst cavity, thus holding it open for delivery of the antibiotic upon inhalation. Direct administration of the drug to the cysts also obviates the need for systemic administration of antibiotics which lead to loss of intestinal flora. This is especially important for individuals with chronic cystic disease who are constantly in danger of developing lung infections due to the presence of mucinous secretions in the cysts and thus are exposed to repeated antibiotic treatment.

Perfluorocarbon may be used in sufficient volume to combine facilitated drug delivery with lung lavage for treatment of cystic disease. If mucinous secretions build up within the cysts, perfluorocarbon can be administered in a volume approaching 100% of the pulmonary functional residual capacity. The powdered antibiotic is then administered by inhalation or forced introduction of a gaseous suspension of microparticles. After sufficient time to allow drug uptake by the lung tissue, any remaining perfluorocarbon may be removed using lavage or other techniques well known in the field of pulmonary treatment. Because the perfluorocarbon is relatively dense compared to mucinous secretions, the perfluorocarbon will tend to displace the secretions in the cysts and subsequent removal of the perfluorocarbon will facilitate simultaneous removal of accumulated mucinous secretions.

Introduction of anticancer agents directly into the lungs by inhalation or positive pressure introduction of a gaseous suspension of microparticles may be used to treat lung tumors. This type of therapy exposes both healthy and tumorous tissue to the anticancer drug, most of which are cytotoxic. Healthy lung tissue can be shielded from the toxic anticancer agent by first treating the patient with surfactant supplements using the perfluorocarbon enhanced delivery method. Then, the anticancer agent may be selectively administered to the tumor area by using the perfluorocarbon enhanced delivery method. Because perfluorocarbons are more dense than water and body tissue they tend to sink or pool into certain portions of the lungs depending on the orientation of the patient. By orienting the patient into a position that favors accumulation of an administered perfluorocarbon near cancerous lung tissue, the introduced powdered anticancer drugs are selectively localized in the tumor-affected area.

The method of combining liquid perfluorocarbon treatment with inhalation or forced introduction of a gaseous suspension of therapeutic compounds has a number of advantages over other forms of drug delivery. The perfluorocarbon-enhanced delivery can be used for medicaments that would otherwise be ineffective or destroyed by delivery systemically. For example, proteins usually cannot be administered orally because they are destroyed in the alimentary tract. Some proteins may invoke severe allergic reactions and shock in the mammalian host if administered systemically such as intramuscularly or intravenously.

Furthermore, by using perfluorocarbon in conjunction with a medicament, the medicament can be directed to particular portions of the lung because of the relative density of perfluorocarbon compared to body tissue. By orienting the patient appropriately, the perfluorocarbon can selectively accumulate in certain alveoli holding them open and thus making them relatively more accessible to the introduced medicament suspension.

In each instance, the amount of drug used should be an effective amount for local or systemic treatment of the targeted condition. Effective amounts of pharmaceuticals can be readily determined either empirically or by consulting standard reference materials.

In addition to enhanced drug delivery, perfluorocarbon liquids can be used to remove endogenous or foreign material from the interior of the lungs. Perfluorocarbon liquid can be substituted for conventional physiological saline solutions used in lavage. Because perfluorocarbons are oxygenatable, they provide oxygen to the person during the treatment allowing for longer and less dangerous lavage procedure. In addition, because some perfluorocarbons have lung surfactant properties, removal of the natural lung surfactant is minimized. The density of perfluorocarbon liquids is generally twice that of water and body tissue which permits the perfluorocarbon to sink below and displace the material to be removed. Then when the perfluorocarbon is removed by mechanical means well known in the practice of lavage, the displaced material will float and be simultaneously removed. These properties are particularly important when lavage is combined with perfluorocarbon-enhanced drug delivery as a complete treatment of, for example, a patient with cystic fibrosis whose lungs accumulate excess mucinous secretions.

The general principles of the present invention may be more fully appreciated by reference to the following non-limiting examples.

EXAMPLE 1

Delivery of Surfactant Supplements

Powdered surfactant supplements are beneficial for treating individuals with lung surfactant deficiencies including premature infants with RDS (born before 36 weeks gestation) and adults with ARDS resulting from lung trauma.

An adult who has ARDS because of burn injury and smoke inhalation resulting from being inside a burning building has severe damage to the lung epithelium and endothelium accompanied by capillary damage. Because of epithelium damage the patient also has decreased surfactant production and foci of collapsed alveoli (atelectasis) leading to localized hypoxia. The patient is treated by using the perfluorocarbon-enhanced delivery method in which the medicament inhaled or introduced by forcing a gaseous microparticulate suspension is a surfactant supplement in powdered form.

The patient is placed on a conventional ventilator and allowed to breath pure oxygen for approximately ten to fifteen minutes. Then perfluorocarbon liquid is introduced into the pulmonary air passages by injecting the liquid into and through an endotracheal tube between breaths of air supplied by continued positive pressure ventilation. The volume of perfluorocarbon liquid introduced into the pulmonary air passages is substantially equivalent to 100% of the normal pulmonary functional residual capacity (FRC) of the patient, calculated by methods well known in the art. The perfluorocarbon liquid introduced is one that has a relatively low vapor pressure because the surfactant supplement must remain in the lungs for a longer period of time (hours). Thus, either one or a combination of PFOB, F-nonmame, FDMA, F-adamatane, F66E, Fi36E, PFoCl and PFoH is administered.

Surfactant supplements consisting of proteins (SP-A, SP-B and SP-C) derived from extracts prepared from human or animal lung lavage are administered by inhalation of a powdered form of the supplement. Another microparticulate therapeutic agent that serves as a lung surfactant includes synthetic mixtures of phospholipids, including a mixture of diphosphatidylcholine and phosphoglycerol in a ratio of 7:3. The powdered surfactant is administered by inhalation where the microparticulate is periodically injected as a fine suspension into the positive pressure ventilation line or via the endotracheal tube at the moment of inspiration. The surfactant is either the proteinaceous type or the phospholipid type or an admixture of both depending on the extent of lung damage as determined by the treating physician. Following inhalation of the surfactant supplement suspension, a second volume of perfluorocarbon liquid is administered to ensure complete dispersion of the surfactant to all lung tissue surfaces. The second volume of perfluorocarbon will also ensure that the alveoli will remain open due to the presence of perfluorocarbon liquid in the alveoli between surfactant supplement treatments.

Depending on the extent of tissue damage the perfluorocarbon-enhanced delivery of surfactant supplement is periodically repeated. As healing progresses and the patient's natural surfactant is replaced by supplemental surfactant, it may be possible to allow the perfluorocarbon to completely evaporate between dosages of the supplemental surfactant. As healing progresses and alveoli remain open even without intra-alveolar perfluorocarbon, subsequent dosages of supplemental surfactant may be inhaled following administration of smaller volumes of perfluorocarbon liquid (0.01% to 10% of the normal FRC of the patient) and/or use of perfluorocarbons with a relatively high vapor pressure, including F44E, FDC, FTPA, FMOQ, FMIQ, FHQ FCHP, FC-75, RM- 101, $C_7F_{15}Br$ and $C_6F_{13}Br$.

In addition to delivery of therapeutics for treating damaged lung tissue, the method can also be used to administer anticancer drugs to a patient suffering from lung cancer. Any of a variety of anticancer drugs that can be formulated into a microparticulate form may be delivered including a chemotherapeutic drugs (eg., adriamycin), a radionuclide (alone or linked to a cancer-specific antibody), and a toxin such a ricin (alone or linked to a cancer-specific antibody).

EXAMPLE 2

Delivery of an Anticancer Drug

A patient suffering from adenocarcinoma in the middle to outer third of the lung that has not metastasized to other sites in the body is treated with powdered doxorubicin-HCl (e.g., Adriamycin™), a cytotoxic agent active against a variety of solid tumors. Doxorubicin is an antibiotic that selectively kills malignant cells and causes tumor regression by binding to nucleic acids.

The patient is first oriented into a position where the tumor-affected area is located at a gravitational low point so that liquid perfluorocarbon will pool selectively around the area. The patient is allowed to breath pure oxygen for approximately ten to fifteen minutes before perfluorocarbon liquid is introduced into the pulmonary air passages under pressure as in liquid breathing. A volume of perfluorocarbon liquid substantially equivalent to 0.1% to 50% of the normal pulmonary FRC of the patient (calculated by methods well known in the art) is introduced. The amount will depend on the size and location of the tumor so that the introduced perfluorocarbon will tend to pool around the cancerous tissue. Unilateral or local delivery (lobar, segmental) may be preferred depending on the location of the tumor.

A perfluorocarbon liquid with a relatively low vapor pressure is used because it must remain in the lungs for a longer period (hours) for effective administration of the chemotherapeutic. Preferred perfluorocarbons include PFOB, F-nonmame, FDMA, F-adamatane, F66E, Fi36E, PFoCl and PFoH, administered alone or in combination.

Freeze-dried powdered doxorubicin is then inhaled at a dosage determined by the physician depending on the size of the tumor to be treated. Generally 10 mg or less per dosage is inhaled and cumulative doses should never exceed 550 $mg/m^2$ because overdosing increases the risk of cardiomyopathy and resultant heart failure. Because doxorubicin also causes severe local tissue necrosis, care must be taken to limit exposure of healthy tissue to the drug. Inhalation of surfactant supplements (see Example 1) may be combined with chemotherapy treatment. By administering surfactant supplements to the entire lung surface before administration of doxorubicin, the healthy tissue may be protected from the anticancer drug's cytotoxicity. By administering surfactant supplements to the entire lung surface after administration of doxorubicin, surfactant lost due to chemical assault of the normal tissue may be replaced in the lung.

The patient remains oriented in the position to promote perfluorocarbon enhanced delivery to the tumor until all of the perfluorocarbon is dissipated by evaporation. Then the patient is allowed to rest normally.

Other antineoplastic antimetabolites, alone or in combination, are also contemplated for use as chemotherapeutics with this method. They include 5-fluor-2,4 (1H,3H)-pyrimidinedione ("5-FU"), vinblastine sulfate (especially for carcinoma that are resistant to other chemotherapeutic agents), and methotrexate (particularly for squamous cell and small cell lung cancers).

Because all antineoplastic antimetabolites are highly toxic, administration should be carefully supervised by a qualified physician with experience in cancer chemotherapy. Administration of chemotherapeutics using this method should be done, at least initially, while the patient is hospitalized to monitor the patient for evidence of toxicity, especially for hemorrhage from the treated site.

A patient with bronchitis associated with flu, cold, or chronic conditions including emphysema has an excess of mucus secretion in the bronchial tree. The accumulated mucous secretions serve as primary sites for growth of bacteria or fungus in infected lungs. Infections that occur in conjunction with respiratory distress may also be treated using the method to enhance delivery of antibiotics.

EXAMPLE 3

Delivery of Antibiotic for Treatment of Infection Associated with Bronchitis

A child hospitalized with severe bronchitis resulting from the flu is treated with amoxicillin trihydrate ("amoxicillin"), a semisynthetic antibiotic with broad spectrum bacteriocidal activity against gram-positive and gram-negative organisms including streptococci, pneumococci, and nonpenicillinase-producing staphylococci. The child is placed on a positive pressure ventilator from which he breathes pure oxygen for about ten to fifteen minutes. Then, perfluorocarbon is introduced into the lungs under pressure as in liquid breathing. A volume of perfluorocarbon liquid substantially equivalent to 0.1% to 50% of the child's normal pulmonary functional residual capacity (calculated by methods well known in the art) is introduced. Perfluorocarbons with a relatively high vapor pressure, including F44E, FDC, FTPA, FMOQ, FMIQ, FHQ FCHP, FC-75, RM-101, $C_7F_{15}Br$ and $C_6F_{13}Br$, are preferred because they will be more readily evaporated by normal or ventilator-assisted breathing after treatment is completed. After the perfluorocarbon has been administered, a dosage of powdered amoxicillin of approximately 1 to 10 mg/kg is introduced into the child's lungs under pressure supplied by the positive pressure ventilator. Evaporation of the perfluorocarbon occurs during ventilator-assisted breathing following antibiotic treatment. Because the antibiotic is delivered to the site of the infection, the amount of antibiotic used is decreased compared to standard oral dosages (40 mg/kg/day in divided dosages every 8 hours).

The same treatment is repeated in a second dosage approximately 8 hours later and thereafter at 8 hour intervals until infection appears to be controlled by the drug. After one or a few treatments using perfluorocarbon enhanced antibiotic delivery, the child can be maintained on standard oral dosages of amoxicillin.

In addition to antibiotics, decongestants (e.g., ephedrine HCl) in microparticulate form may be included in the introduced antibiotic dosage to limit mucus secretions. Additionally, if there is evidence of infectious injury to the lung tissue, surfactant supplements (see Example 1) may be included during inhalation of the antibiotic.

Immunocompromised patients such as those affected by AIDS or those taking immunosuppressive drugs to avoid transplant rejection are unusually susceptible to infections including pulmonary infections. The perfluorocarbon-enhanced drug delivery method may be used to treat such patients.

EXAMPLE 4

Treatment of Immunocompromised Patient for Lung Infection

An adult with AIDS presents at an emergency facility with a high grade fever and bronchial congestion indicating that he has a pulmonary infection. He is treated with amoxicillin using perfluorocarbon-enhanced delivery as in Example 3 except that the perfluorocarbon liquid is introduced before and after introduction of an adult dosage of powdered amoxicillin of approximately 10 to 100 mg every 8 hours. Because of his immunocompromised state and greater potential for alveolar collapse resulting from his weakened condition, introduction of the perfluorocarbon liquid before introduction of the antibiotic will ensure that alveoli are open. Introduction of perfluorocarbon liquid after introduction of the antibiotic will ensure complete dispersal of the antibiotic to all lung tissue. A volume of perfluorocarbon liquid substantially equivalent to 50% of his normal pulmonary functional residual capacity (calculated by methods well known in the art) is introduced at both times. Following a day or two of perfluorocarbon-enhanced delivery of amoxicillin, he is switched to oral dosages of 500 mg every 8 hours for approximately 8 to 10 days.

Alveolar macrophages are phagocytic cells that migrate into the lungs in response to irritation where they engulf and remove foreign objects such as bacteria or foreign particles. Perfluorocarbon-enhanced treatment with agents that increase activity of alveolar macrophages speeds removal of foreign irritants in the lungs.

EXAMPLE 5

Delivery of Immunologically Active Factors to Enhance Pulmonary Macrophage Activity Cell-mediated immunity depends on cells called macrophages that attack foreign objects and pathogens by engulfing them and removing them from the body through proteolytic digestion and physical removal to the lymphatic system. Macrophages migrate into the lungs when foreign irritants are present. Macrophages are activated by lymphokines which are proteins produced by certain classes of T cells. This process can be painfully slow because it involves a cascade of events: macrophages engulf the foreign invader and partially digest it; macrophages present antigens derived from the invader on their cell surface; these antigens are then recognized by antigen-specific T-cells which in turn produce lymphokines to solicit migration of other phagocytic cells to the site.

By delivering identified macrophage-activating lymphokines to the lungs shortly after exposure to bacterial or particulate irritants, the process of macrophage-mediated removal is increased and removal of the irritant occurs more rapidly. Interleukin-2 (IL-2) is a multifunctional lymphokine that enhances macrophage activity.

A worker in a chemical processing plant who has been exposed to a large amount of particulate irritant as a result of an industrial accident presents with severe respiratory distress. The patient's lungs are first treated by lavage with perfluorocarbon liquid (using a volume equal to 100% of the patient's pulmonary FRC) using lavage techniques well known in the field to remove the majority of easily dislodged particulates. The perfluorocarbon liquid is mechanically removed by using standard lavage techniques. Then the patient is treated with powdered IL-2 using the perfluorocarbon-enhanced delivery method.

The patient is placed on a conventional ventilator and allowed to breath pure oxygen for approximately ten to fifteen minutes before perfluorocarbon liquid is introduced into the pulmonary air passages by injecting the liquid into and through an endotracheal tube between breaths. The volume of perfluorocarbon liquid introduced is substantially equivalent to 100% of the normal pulmonary FRC of the patient as calculated by methods well known in the art. The perfluorocarbon liquid introduced is one that has a relatively low vapor pressure because the surfactant supplement may remain in the lungs for a period of hours. Thus, either one or a combination of PFOB, F-nonmame, FDMA, F-adamatane, F66E, Fi36E, PFoCl and PFoH is administered.

IL-2 is administered by introduction of a microparticulate form that is injected as a fine suspension into the positive pressure ventilation line or via the endotracheal tube during a positive pressure ventilation. Other microparticulate therapeutic agents that serve as lung surfactant supplements (see Example 1) may also be included if the treating physician suspects damage to the surfactant or underlying tissue caused by inhalation of the chemical particles or the subsequent lavage. Multiple inhalations of IL-2 and surfactant supplements may be made while the perfluorocarbon remains in the lung. Alternatively, a single inhalation of IL-2 may be followed with multiple inhalations of surfactant supplement to maintain the alveolar surface during phagocytosis of the foreign particles.

Following treatment, the perfluorocarbon dissipates by evaporation during normal breathing.

Acute inflammation of the lungs that occurs following exposure to noxious or allergic-reaction producing particles may be treated with perfluorocarbon-enhanced delivery of immunosuppressive drugs.

EXAMPLE 6

Treatment of Acute Inflammatory Reaction by Delivery of Immunosuppressive Drug

When macrophages and polymorphonuclear cells rapidly invade pulmonary tissue in response to exposure to noxious or virulent particle, the lungs become inflamed leading to much discomfort and breathing difficulty. Immunosuppressive drugs including anti-inflammatory steroids are often used to decrease inflammation. Dispersal of the anti-inflammatory steroids into the lungs is critical to relieve the symptoms.

A person exposed to a massive dose of pollen suffers a severe allergic reaction and extreme difficulty breathing. The person presents at an emergency facility and is treated with microparticulate flunisolide (6α-fluoro-11β, 16α, 17, 21-tetrahydroxypregna-1, 4-diene-3, 20 dione cyclic-16, 17-acetyl with acetone) by using the perfluorocarbon enhanced delivery method.

Because acute inflammation results in severely restricted ability to breath, the patient is placed on a positive pressure ventilator from which he breathes pure oxygen for about ten to fifteen minutes. Then, a dosage of 0.25–0.5 mg of flunisolide, a corticosteroid with marked anti-inflammatory and anti-allergic activity perfluorocarbon is introduced into the lungs under pressure supplied by the ventilator as described in Example 5. Then perfluorocarbon liquid is introduced into the lungs under pressure as in liquid breathing or via an endotracheal tube between breaths of air supplied by continued positive pressure ventilation. A volume of perfluorocarbon liquid substantially equivalent to 0.1% to 100% of the patient's normal pulmonary functional residual capacity (calculated by methods well known in the art) is introduced, depending on the degree of alveolar constriction. Perfluorocarbons with a relatively high vapor pressure, including F44E, FDC, FTPA, FMOQ, FMIQ, FHQ FCHP, FC-75, RM-101, $C_7F_{15}Br$ and $C_6F_{13}Br$, are preferred because they will be more readily evaporated by normal or ventilator-assisted breathing after treatment is completed. The flunisolide dosage administered is 0.25–0.5 mg and may be repeated approximately 10–12 hours later if necessary. Because the drug is readily dispersed to the alveoli by introduction of the perfluorocarbon liquid, the flunisolide dosage required is less than required by patients using standard self-administered aerosol inhaler systems. After therapy is completed, the patient is maintained on perfluorocarbon for up to 3 hours to keep alveoli open if inflammation does not subside quickly. When inflammation subsides, the perfluorocarbon is allowed to dissipate by evaporation during breathing.

Use of the method with other anti-inflammatory agents including triamcinolone (9-fluoro-11β, 16α, 17,21 -tetrahydroxypregna-1,4-diene-3,20-dione), triamcinolone acetonide (9-fluoro-11β, 16α, 17,21-tetrahydroxypregna-1,4 -diene-3,20-dione cyclic 16, 17-acetal), beclomethasone dipropionate (9-chloro-11β, 17,21-trihydroxy-16β -methylpregna-1,4-diene-3,20-dione 17,21-dipropionate), betamethasone sodium phosphate (9-fluoro-11β, 17,21 -trihydroxy-16β-methylpregna-1,4-diene-3,20-dione 21-sodium phosphate), hydrocortisone (pregna-4-ene-3,20-dione, 21 (acetyloxy)-11, 17-dihydroxy-acetate), dexamethasone sodium phosphate (9-fluoro-11β, 17-dihydroxy-16α-methyl-21 -(phosphono-oxy)pregna-1,4-diene-3,20-dione 17,21-disodium salt), and triamcinolone acetonide (9-fluoro-11β, 16α, 17,21 -tetrahydroxypregna-1,4-diene-3, 20-dione-cyclic 16,17-acetal), is also contemplated.

Because hyaline membranes substantially interfere with gaseous exchange in the lungs associated with ARDS and hyaline membrane disease in infants, dissolving hyaline membranes increases the patient's ability to utilize oxygen and excrete carbon dioxide.

EXAMPLE 7

Delivery of Enzymes to Dissolve Hyaline Membranes

Hyaline membranes contain protein-rich, fibrin-rich edematous fluid admixed with cellular debris. As such they are degraded by enzymes that dissolve proteins and cellular debris including nucleic acids. Perfluorocarbon-enhanced delivery of proteinases and deoxyribonuclease dissolves hyaline membranes making them more easily removed by normal cellular (i.e., macrophage) action.

An adult with ARDS accompanied by hyaline membrane formation and foci of collapsed alveoli (atelectasis) is put on a positive pressure ventilator using standard practices. After being allowed to breath pure oxygen for approximately ten to fifteen minutes, perfluorocarbon liquid is introduced into the pulmonary air passages by injecting the liquid into and through an endotracheal tube between breaths of air supplied by continued positive pressure ventilation. Perfluorocarbon liquid equivalent to approximately 100% of the normal pulmonary FRC of the patient (calculated by well known methods) is introduced into the pulmonary air passages. The perfluorocarbon liquid introduced is one that has a relatively low vapor pressure because the surfactant supplement must remain in the lungs for a longer period of time (hours). Thus, either one or a combination of PFOB, F-nonmame, FDMA, F-adamatane, F66E, Fi36E, PFoCl and PFoH is administered.

A combination of a proteinase, fibrinolysin, and deoxyribonuclease, both in powder form, are introduced by inhalation of the microparticles. Fibrinolysin is derived from bovine plasma and primarily digests fibrinous exudates; deoxyribonuclease is derived from bovine pancreas and attacks deoxyribonucleic acid (DNA) to produce large polynucleotides. Dosage of the enzyme combination is 5–25 units (Loomis) of fibrinolysin and 3,000–15,000 units (Christensen) of deoxyribonuclease, depending on the extent of hyaline membrane formation in the patient's lungs. The powdered enzymes are administered by inhalation where the powder is periodically injected as a fine suspension into the positive pressure ventilation line or via the endotracheal tube.

If the patient also suffers from loss of surfactant due to hyaline-membrane induced hypoxia, surfactant supplement (see Example 1) may be included in the enzyme inhalation mixture. The synthetic phospholipid type of surfactant supplement is preferred because the proteinaceous type would serve as a competitive inhibitor of the proteinase in the enzyme mixture. Alternatively, either the protein or phospholipid type of surfactant supplement may be used subsequent to inhalation of the enzyme combination. Proteinaceous surfactant supplement could be used to "stop" the activity of the enzyme mixture by competitively inhibiting the fibrinolysin.

Depending on the extent of tissue damage from hypoxia the perfluorocarbon liquid is periodically replaced to open collapsed alveoli during healing because evaporation will decrease the volume of retained perfluorocarbon. As healing progresses, the perfluorocarbon is allowed to completely evaporate through normal breathing, with or without mechanical ventilation.

Perfluorocarbon-enhanced drug delivery may be used to treat tuberculosis, a disease which is increasing in frequency in the U.S.

EXAMPLE 8

Treatment of Tuberculosis by Localized Delivery of Anti-Inflammatory Antibacterial The perfluorocarbon-enhanced method is used for delivery of the sodium salt of mephenamine in microparticulate form. The drug serves as a local anti-inflammatory with bacteriostatic and bacteriocidal activities, including bacteriostasis of tubercule bacillus. Powdered streptomycin sulfate, effective against most forms of drug-resistant tuberculosis, may also be included in the inhaled therapeutic.

The patient diagnosed with tuberculosis is first oriented into a position where the affected area (determined by X rays or other non-invasive diagnostic means) is located at a gravitational low point so that perfluorocarbon pools selectively around the area. The patient is allowed to breath pure oxygen for approximately ten to fifteen minutes before perfluorocarbon liquid is introduced into the pulmonary air passages under pressure as in liquid breathing. A volume of perfluorocarbon liquid substantially equivalent to 0.1% to 100% of the patient's normal FRC (calculated by methods well known in the art) is introduced. The amount will depend on the location and area affected by the infection so that the introduced perfluorocarbon will tend to pool around the infected tissue. Unilateral or local delivery (lobar, segmental) may be preferred depending on the extent of the infection.

A perfluorocarbon liquid with a relatively low vapor pressure is used because it must remain in the lungs for a longer period (hours) for effective administration of the antibacterial agents. Preferred perfluorocarbons include PFOB, F-nonmame, FDMA, F-adamatane, F66E, Fi36E, PFoCl and PFoH, administered alone or in combination.

A powdered therapeutic comprising one or more antibacterials (e.g., sodium mephenamine combined with streptomycin sulfate) is inhaled by the patient. The patient is not moved for a period up to three hours to allow the antibacterials to be absorbed by the affected tissue. During that time, normal breathing will result in evaporation of the perfluorocarbon liquid. Treatment may be repeated weekly for a period of months with systemic antibiotics administered between treatments to help clear the infection.

In addition to diseases that directly affect the lungs, the perfluorocarbon-enhanced drug delivery method may be used to deliver drugs for other therapeutic purposes.

EXAMPLE 9

Treatment of Pulmonary Emboli by Inhalation of Powdered Urokinase After Perfluorocarbon Infusion Occlusion of a pulmonary artery by blot clot leads to arterial obstruction. Obstruction may lead to infarction of the underlying lung parenchyma. Sudden death may occur in the case of a saddle embolus where the obstruction is at the major branches of the pulmonary arteries and blood flow through the lungs ceases.

Urokinase injected intravenously is often used to promote lysis of pulmonary embolism. Urokinase, an enzyme produced by the kidney, acts on the endogenous fibrinolytic system. It converts plasminogen to the enzyme plasmin which degrades fibrin clots as well as plasminogen and other plasma proteins. However, intravenously injected urokinase has a half-life of about 20 minutes or less because it is rapidly degraded by the liver. Furthermore, systemic injection of urokinase is contraindicated in cases in which there has been recent surgery or gastrointestinal bleeding.

A patient with a pulmonary embolism may be treated using the perfluorocarbon-enhanced drug delivery method where the urokinase is inhaled as a powder (the low molecular weight form which may also contain inert carriers such as mannitol, albumin and sodium chloride).

Depending on the location of the embolism, the patient is oriented so that the embolism is located at a gravitational low point. Then the patient is allowed to breath pure oxygen for approximately ten to fifteen minutes. Perfluorocarbon liquid is introduced into the pulmonary air passages under pressure as in liquid breathing. The volume of perfluorocarbon liquid introduced into the pulmonary air passages is substantially equivalent to 0.1% to 100% of the normal pulmonary FRC of the patient calculated by methods well known in the art. The amount will depend on the size and location of the embolism so that the introduced perfluorocarbon will tend to pool in the area near the embolism. Unilateral or local delivery (lobar, segmental) may be preferred depending on the location in which the perfluorocarbon should settle. The perfluorocarbon liquid introduced is one that has a relatively high vapor pressure because the urokinase will be introduced rapidly. If pulmonary infarction has already occurred and alveoli are collapsed, a low vapor pressure perfluorocarbon may be used to simultaneously open the alveoli.

After the perfluorocarbon has settled into the area of the embolism, a single dose of powdered urokinase is inhaled and the patient is allowed to breath normally so that remaining perfluorocarbon is evaporated. The patient is monitored for hemolysis in the lung and surfactant supplements (see Example 1) may be included in the urokinase dosage to protect pulmonary tissue during administration. Because enhanced delivery of the urokinase occurs at a region near the embolism, the concentration is higher near the site where activity is needed. Hence, problems associated with internal bleeding resulting from systemic delivery are overcome.

Chronic conditions such as accumulation of mucinous secretions in the lungs of people afflicted with cystic fibrosis may also be treated by using the method, where the perfluorocarbon liquid serves the additional function of removing excess secretions by lavage prior to drug delivery.

EXAMPLE 10

Treatment of Cystic Fibrosis by Removal of Excess Mucinous Secretions from Lungs and Administration of Powdered Enzymes A adolescent with cystic fibrosis periodically experiences difficulty breathing because cavities in her lungs are filled with mucinous secretions. This condition frequently leads to infection of the cysts, especially by Streptococcus bacteria. Accumulation of secretions also makes her lung epithelium lining susceptible to progressive metaplasia which may result in necrosis and a lung abscess. Therefore it is advantageous to periodically clear her lungs of excess mucinous secretions to facilitate easier breathing and prevent infections, and to administer dosages enzymes as in Example 7 to clear residual accumulated secretions. Because cystic fibrosis leads to deterioration of the lungs' elastic and reticulin fibers that predisposes the tissue to rupture, it is important also to both relieve inhalation stress on the cystic tissue.

The adolescent who is currently experiencing breathing difficulty due to accumulation of mucinous secretions in her lungs is first treated with perfluorocarbon liquid as a lavage to remove some of the excess secretions. She is placed on a conventional ventilator and allowed to breath pure oxygen for approximately ten to fifteen minutes. Then oxygenated perfluorocarbon liquid is introduced into her pulmonary air passages under pressure as for liquid breathing. The volume of perfluorocarbon liquid introduced into the pulmonary air passages is substantially equivalent to 100% of her normal pulmonary FRC, calculated by methods well known in the art. The perfluorocarbon liquid introduced is one that has a relatively low vapor pressure because it will be removed mechanically and evaporation should be minimized. Thus, either one or a combination of PFOB, F-nonmame, FDMA, F-adamatane, F66E, Fi36E, PFoCl and PFoH is administered. After sufficient time for the perfluorocarbon liquid to infuse her lungs (up to an hour) and displace accumulated secretions, the perfluorocarbon and displaced secretions are removed mechanically using conventional lavage procedures.

After lavage is completed, the adolescent is administered a second volume of perfluorocarbon liquid under pressure as for liquid breathing. The volume and type of perfluorocarbon liquid are substantially as used in the lavage procedure. Then a dosage of powdered proteolytic and deoxyribonuclease enzymes as in Example 7 is introduced using positive pressure supplied by a ventilator. The enzymes will clear any residual mucinous secretions that remain after lavage. The patient is allowed to rest while her breathing is assisted by a positive pressure ventilator until all remaining perfluorocarbon has evaporated (up to about three hours).

I claim:

1. A method for pulmonary drug delivery, comprising the steps of:

introducing into pulmonary air passages of a mammalian host a volume of perfluorocarbon liquid substantially equivalent to or less than the pulmonary functional residual capacity of the host;

dispersing a microparticulate medicament in a breathable gas to form a gas/medicament dispersion; and introducing said dispersion into the pulmonary air passages containing the introduced perfluorocarbon liquid, such that said perfluorocarbon liquid and said microparticulate medicament are simultaneously present in the same pulmonary air passages of the host.

2. The method of claim 1, wherein said volume of said perfluorocarbon liquid is introduced prior to the introduction of said dispersion.

3. The method of claim 2, further comprising the step of introducing a second volume of perfluorocarbon liquid into the pulmonary air passages of the host subsequent to administration of said dispersion.

4. The method of claim 1, wherein said dispersion is introduced prior to introduction of said perfluorocarbon liquid.

5. The method of claim 4, wherein lavage with a perfluorocarbon liquid is performed prior to introduction of said dispersion.

6. The method of claim 1, further comprising, after the steps of introducing perfluorocarbon liquid and introducing said dispersion, a step of removing the perfluorocarbon liquid from the pulmonary air passages.

7. The method of claim 6, wherein the perfluorocarbon liquid is removed from the pulmonary air passages by evaporation.

8. The method of claim 6, wherein the perfluorocarbon liquid is removed from the pulmonary air passages by mechanical means.

9. The method of claim 1, wherein the volume of perfluorocarbon liquid is equivalent to 0.01% to 100% of the pulmonary functional residual capacity of the host.

10. The method of claim 1, wherein the volume of perfluorocarbon liquid is at least 1% of the pulmonary functional residual capacity of the host.

11. The method of claim 1, wherein the volume of perfluorocarbon liquid is at least 5% of the pulmonary functional residual capacity of the host.

12. The method of claim 1, wherein the volume of perfluorocarbon liquid is at least 10% of the pulmonary functional residual capacity of the host.

13. The method of claim 1, wherein the volume of perfluorocarbon liquid is at least 20% of the pulmonary functional residual capacity of the host.

14. The method of claim 1, wherein the volume of perfluorocarbon liquid is not more than 75% of the pulmonary functional residual capacity of the host.

15. The method of claim 1, wherein the volume of perfluorocarbon liquid is not more than 50% of the pulmonary functional residual capacity of the host.

16. The method of claim 1, wherein the volume of perfluorocarbon liquid is not more than 30% of the pulmonary functional residual capacity of the host.

17. The method of claim 1, wherein the volume of perfluorocarbon liquid is not more than 20% of the pulmonary functional residual capacity of the host.

18. The method of claim 1, wherein the medicament is an anticancer agent.

19. The method of claim 1, wherein the medicament is a surfactant supplement.

20. The method of claim 1, wherein the medicament is at least one enzyme.

21. The method of claim 20, wherein said enzyme is a proteinase.

22. The method of claim 20, wherein said enzyme is a deoxyribonuclease.

23. The method of claim 1, wherein the medicament enhances activity of the immune system of the host.

24. The method of claim 1, wherein the medicament is an immunosuppressor.

25. The method of claim 1, wherein the medicament is a decongestant.

26. The method of claim 1, wherein the medicament is selected from the group consisting of antibiotics, antivirals, antibacterials and combinations thereof.

27. The method of claim 1, wherein the medicament is capable of translocation across pulmonary membranes to affect systemic administration.

28. A method for the pulmonary administration of pharmaceutical compounds, comprising the steps of:

dispersing a microparticulate medicament in a breathable gas to form a gaseous pharmaceutical suspension;

introducing said gaseous pharmaceutical suspension into pulmonary air passages of a mammalian host; and subsequently introducing a volume of perfluorocarbon liquid substantially equivalent to or less than the pulmonary functional residual capacity of the mammalian, such that said perfluorocarbon liquid and said microparticulate medicament are simultaneously present in the same pulmonary air passages of the host.

29. A method of pulmonary drug delivery providing enhanced bioavailability, said method comprising the steps of:

performing lavage on a mammalian host using a liquid perfluorocarbon wherein endogenous or foreign material is removed from pulmonary air passages of host;

dispersing a microparticulate medicament in a breathable gas to form a gaseous pharmaceutical suspension;

introducing said gaseous pharmaceutical suspension into pulmonary air passages of a mammalian host; and subsequently introducing a volume of perfluorocarbon liquid substantially equivalent to or less than the pulmonary functional residual capacity of the mammalian host, such that said perfluorocarbon liquid and said microparticulate medicament are simultaneously present in the same pulmonary air passages of the host.

* * * * *